United States Patent [19]

Horrobin

[11] Patent Number: 5,562,913
[45] Date of Patent: Oct. 8, 1996

[54] FORMULATION FOR USE IN SMOKERS

[75] Inventor: David F. Horrobin, Guildford, England

[73] Assignee: Scotia Holdings PLC, England

[21] Appl. No.: 214,553

[22] Filed: Mar. 18, 1994

[30] Foreign Application Priority Data

Mar. 19, 1993 [GB] United Kingdom .................. 9305737
May 10, 1993 [GB] United Kingdom .................. 9309596

[51] Int. Cl.$^6$ ............... A61K 7/00; A61K 7/06; A61K 9/20; A61K 9/48
[52] U.S. Cl. .................. 424/401; 424/436; 424/447; 424/456; 424/464; 424/489; 424/701; 424/DIG. 5; 514/560; 514/945
[58] Field of Search ................. 424/401, 436, 424/447, 456, 464, 489, 701, DIG. 5; 514/560, 945

[56] References Cited

U.S. PATENT DOCUMENTS 5,158,975  10/1992  Guichardant et al. .................. 514/560

FOREIGN PATENT DOCUMENTS

| 59115/90 | 1/1991 | Australia . |
| 62135/90 | 3/1991 | Australia . |
| 44748/93 | 2/1994 | Australia . |
| 901390 | 6/1985 | Belgium . |
| 0334507 | 9/1989 | European Pat. Off. . |
| 73.32114 | 3/1974 | France . |
| 2597337 | 10/1987 | France . |
| 2609630 | 7/1988 | France . |
| 1446431 | 8/1976 | United Kingdom . |
| 2151924 | 7/1985 | United Kingdom . |
| 90/11073 | 10/1990 | WIPO . |
| 91/17670 | 11/1991 | WIPO . |
| 93/06812 | 4/1993 | WIPO . |

OTHER PUBLICATIONS

Database WPI Derwent AN 90103141 & JP–A–2 053 706 Feb. 1990 (Croda Japan KK).
Database WPI Derwent AN 88366123 & JP–A–63 277 604 Nov. 1988 (Showa Denko KK).
Int. J. Cosmet. Sci. vol. 3, No. 2, 1981 pp. 83–94 Costedoat et al "Absorption et distribution de l'acide gamma–. . . ".
J. Natl. Cancer Inst. vol. 177, No. 5, 1986 pp. 1053–1062 Begin et al "Differential Killing of Human Carcinoma . . . ".
Lancet vol. 1, No. 8284, Jun. 1982 pp. 1269–1272 Hay et al "Effect of Fish Oil on Platelet Kinetics in Patients . . . ".
Patent Abstracts of Japan vol. 11, No. 365 (C–460) (2812) Nov. 1987 & JP–A–62 138 411 (Kanebo Ltd).
JNCI, vol. 77, No. 5, Nov. 1986 pp. 1053–1061 Begin et al "Differential Killing of Human Carcinoma Cells Supplemented with n–3 and n–6 Polyunsaturated Fatty Acids" .
The Lancet Jun. 5, 1982 pp. 1269–1272 Hay et al "Effect of Fish Oil on Platelet Kinetics in Patients with Ischaemic Heart Disease".

*Primary Examiner*—Jyothsna Venkat
*Attorney, Agent, or Firm*—Nixon & Vanderhye

[57] ABSTRACT

Preparation of a formulation for mitigating ill effects of smoking, wherein one or more of the n-6 EFAs selected from GLA, DGLA and AA, and one or more of the n-3 EFAs selected from SA, 20:4n-3, EPA, DPA or DHA are used, preferably so that the daily dose of each fatty acid is within the range 1 mg to 100g/day. The formulation may in many other purposes be used in the treatment or prevention of ageing of the skin of smokers.

9 Claims, No Drawings

FORMULATION FOR USE IN SMOKERS

Smoking is established as a major factor in many different health problems but particularly in lung cancer, in chronic lung problems such as bronchitis, and in coronary and peripheral arterial disease. However, despite a great deal of work, the mechanism of smoking-induced damage has not been adequately elucidated. Moreover there are important anomalies in the association between smoking and disease. For example, although cigarettes smoked in Japan are similar to those elsewhere, and although the physiological and biochemical changes induced by smoking are similar in Japanese and in other people, smoking seems much less harmful in Japan than it is in other countries. There has been no adequate explanation for this.

As part of an investigation on peripheral vascular disease, 120 normal individuals between the ages of 40 and 70, and 120 patients with peripheral vascular disease completed a detailed questionnaire on their smoking habits. As a result an estimate was made for each person of lifetime consumption of cigarettes. This was related to the severity of peripheral vascular disease using the ankle/brachial pressure index (ABPI) as a measure. In a normal individual in the supine position, the blood pressure at the ankle and in the arm is identical and the index ankle pressure/arm pressure is 1.0. With increasing severity of arterial disease which almost invariably affects the leg arteries more than the arm, the pressure at the ankle falls below that in the arm. The ABPI is therefore a measure of the severity of blockage of the leg arteries.

The lifetime number of cigarettes smoked was found to be inversely related to the ABPI. The greater the amount of smoking the greater was the blocking of the femoral artery, the main artery to the leg. The relationship was very highly significant ($P<0.001$). This observation supported much earlier work linking smoking to arterial disease.

Blood samples were taken from all individuals in the study. The lipids were extracted from plasma and separated into phospholipid, cholesterol ester and triglyceride tractions by thin layer chromatography. Each fraction was then methylated and the composition of the resulting fatty acid methyl esters measured by quantitative gas chromatography. The essential fatty acids were measured and their concentrations related to lifetime smoking by Spearman's rank correlation. The significance and direction of the correlations are summarised in Table 1.

Correlations were made between smoking habit (lifetime estimate of total cigarettes smoked) and levels or certain essential fatty acids in plasma lipid fractions. Each value is the statistical significance of the relationship using Spearman's rank correlation. All correlations were negative, the greater the degree of smoking, the lower the fatty acid level (ns=not significant)

TABLE 1

| | | |
|---|---|---|
| Linoleic | triglyceride | $p < 0.05$ |
| | cholesterol ester | $p < 0.05$ |
| | phospholipid | ns |
| Arachidonic | triglyceride | $p < 0.05$ |
| | cholesterol ester | $p < 0.05$ |
| | phospholipid | ns |
| Eicosapentaenoic | triglyceride | $p < 0.05$ |
| | cholesterol ester | $p < 0.001$ |
| | phospholipid | $p < 0.1$ |
| Docosahexaenoic | triglyceride | $p < 0.05$ |
| | cholesterol ester | $p < 0.001$ |
| | phospholipid | $p < 0.001$ |

It can be seen that smoking is associated with a lowering of the levels of linoleic acid in all fractions. The lowering of linoleic acid levels by smoking has been well documented previously. However, also lowered by smoking are the concentrations of arachidonic acid (AA), eicosapentaenoic acid (EPA), docosapentaenoic acid (DPA n-3) and docosahexaenoic acid (DHA) and this is a new finding.

We believe that lack of these four long chain highly unsaturated fatty acids plays an important role in the adverse effects of smoking. The acids certainly play several vital functions in the body, being important constituents of every cell membrane, modulators of many second messenger systems, and sources of other second messengers such as prostaglandins and leukotrienes. Of particular interest is the fact that while these four acids are present in only modest amounts in the diet in most countries, in Japan they are present at high levels. AA, EPA, n-3 DPA and DHA are found in substantial amounts in oily fish which form a much more important pan of the Japanese diet than is the case in other countries. Thus a Japanese who smokes but who eats a traditional Japanese diet will not suffer the same biochemical consequences of smoking as a person in other countries. The long chain essential fatty acids are formed within the body via the sequence of reactions shown in Table 2:

TABLE 2

| n-6 | n-3 |
|---|---|
| 18:2 delta-9,12 (linoleic acid) | 18:3 delta-9,12,15 (alpha-linolenic acid) |
| delta-6 desaturase ↓ | |
| 18:3 delta-6,9,12 (gamma-linolenic acid) | 18:4 delta-6,9,12,15 (stearidonic acid) |
| elongation ↓ | |
| 20:3 delta-8,11,14 (dihomo-gamma-linolenic acid) | 20:4 delta-8,11,14,17 |
| delta-5 desaturase ↓ | |
| 20:4 delta-5,8,11,14 (arachidonic acid) | 20:5 delta-5,8,11,14,17 (eicosapentaenoic acid) |
| elongation ↓ | |
| 22:4 delta-7,10,13,16 (adrenic acid) | 22:5 delta-7,10,13,16,19 |
| delta-4 desaturase ↓ | |
| 22:5 delta-4,7,10,13,16 | 22:6 delta-4,7,10,13,16, 19 (docosahexaenoic acid) |

The acids, which in nature are of the all-cis configuration, are systematically named as derivatives of the corresponding octadecanoic, eicosanoic or docosanoic acids, e.g. delta-9, 13-octadecadienoic acid or delta4,7, 10, 13, 16, 19-docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 1 8:3 n-3 has a commonly used trivial name, alpha-linolenic acid, though the name stearidonic acid is coming into use for the 18:4 n-3 acid and the names eicosapentaenoic acid and docosahexaenoic acid as such are also used.

The main dietary essential fatty acids are thus linoleic acid (LA) and alpha-linolenic acid (ALA), which are converted to the higher acids by a series of alternating desaturation and elongation reactions. The first step in this reaction is however very slow and rate limiting, and it is not usually possible to change the levels of the long chain acids by changing intakes of LA and ALA. However it is possible to change the levels of the four particular long chain acids that are low in smokers by by-passing the first rate-limiting step by giving GLA, DGLA or AA in the case of the n-6 EFAs, or stearidonic acid (SA), the 20:4n-3 acid, EPA, DPA or DHA in the case of the n-3 EFAs. In smokers, it will therefore be possible to correct the deficits found in EFA levels by providing one or more of each of these groups of specific n-6 and n-3 EFAs, as illustrated in the examples. The value of those EFAs for smokers may be described on the labelling of the packs in which the EFAs are provided or in associated literature.

The long chain essential fatty acids whose levels are reduced by smoking are particularly important in the skin. The skin may be supplied with these fatty acids either via the bloodstream or via topical application. One of the most important actions of smoking is its ability to produce accelerated skin ageing. The reduced levels of 20 and 22-carbon EFAs in smokers are likely to be very important in this respect.

Therefore, the invention provides for the use of one or more of the n-6 EFAs selected from GLA, DGLA and AA, and/or one or more of the n-3 EFAs selected from SA, 20:4n-3, EPA. DPA or DHA in the preparation of a formulation for mitigating ill effects of smoking, preferably so that the daily dose of each fatty acid is within the range of ling to 100 g/day. The invention also provides for a use of one or more n-6 EFAs, selected from GLA, DGLA and AA, and/or one or more n-3 EFAs selected from SA, 0:4n-3, EPA. DPA or DHA in the preparation of a formulation for treating or preventing ageing of the skin in smokers, preferably so that the daily dose of each fatty acid is within the range ling to 100g per day.

The invention further provides a method of mitigating the ill effects of smoking by correcting the deficits of EFSs in smokers, wherein there is administered to a smoker, one or more of the n-6 EFAs selected from GLA, DGLA and AA, and/or one or more of the n-3 EFAs selected from SA, 20:4n-3, EPA, DPA or DHA, preferably so that the daily dose of each fatty acid is within the range of ling to 100 g/day.

The EFAs may optionally be combined with other nutrients, known to be of value in smokers, such as vitamin C, vitamin E, beta-carotene, the B group of vitamins, calcium and selenium.

Pharmaceutical or nutritional supplement formulations may be prepared so that the smoker receives ling to 100 g per day of each fatty acid, preferably 10 mg to 10 g, very preferably 50 mg to 4 g, and ideally 100 mg to 2 g. Alternatively, either topical preparations or foodstuffs may be prepared containing 0.001 to 50 wt. % of the fatty acids in total, and used by smokers.

The fatty acids may be in any appropriate form including the free acids, any appropriate salts the mono-, di-, or triglycerides, any appropriate ester including cholesterol esters, amides or phospholipids.

The following generally suitable formulations exemplify the invention in themselves or in use to mitigate ill effects of smoking.

EXAMPLES

1. For use by smokers, soft gelatin capsules or hard gelatin capsules, or pastilles or tablets or other pharmaceutical or nutritional dosage forms containing 100 mg GLA, 100 mg AA, 100 mg EPA and 100 mg DHA.

2. Granules or powder for use by smokers, made with gum acacia, gelatin, starch or other appropriate material containing by weight in each gram 50 mg of DGLA, 50 mg AA, 50 mg SA and 50 mg DHA.

3. Oils for use by smokers for use as salad oils or for incorporation into any appropriate food material containing 10% by weight GLA, 5% by weight AA. 5% by weight EPA and 5% by weight DHA.

4. Whips, foams, creams, mousses or other liquid or semi-liquid formulations for use by smokers for use as foods and containing 2% by weight GLA, 2% AA, 2% DGLA. 2% SA, 2% EPA and 2% DHA.

5. Creams, ointments, lotions, shampoos, patches, sticks, pessaries, suppositories or any other dosage form for use by smokers for topical application in which the active material is an oil containing 5% by weight DGLA, 2% AA, 3% EPA and 3% DHA.

6–10. Formulations as in 1–5 for use by smokers in which the active ingredients are any one or more than one of the n-6 EFAs selected from GLA, DGLA and AA, and any one or more than one of the n-3 EFAs selected from SA, 20:4n-3, DPA, EPA or DHA.

11–15. Formulations as in 1–5 for use by smokers in which the active ingredients are either GLA or DGLA of the n-6 series and either EPA or DHA or both of the n-3 series.

16–30. Formulations or foods as in 1–5 for use by smokers in which in addition to the EFAs them are incorporated other essential nutrients, including vitamins and minerals, but particularly vitamin C (in the amount 20 to 2000 mg per day), B group vitamins, vitamin E (in the amount 10 to 2000 international units per day), B-carotene, and bioavallable zinc and selenium. 31–60. Formulations as in 1–30 in which either the n-6 or the n-3 EFAs am present, but not both.

I claim:

1. A method of treating n-6 or n-3 essential fatty acid deficits in smokers wherein there is administered to a smoker a formulation comprising:
   (a) at least one of the n-6 essential fatty acids selected from the group consisting of gamma-linolenic acid (GLA), dihomo-gamma-linolenic acid (DGLA) and arachidonic acid (AA); or
   (b) at least one n-3 essential fatty acid selected from the group consisting of stearidonic acid (SA), 8,11,14-17-eicosatetraenoic acid (20:4n-3), eicosapentaenoic acid (EPA), docosapentaenoic acid (DPA) and docosahexaenoic acid (DHA); or
   (c) a mixture of (a) and (b);
so that the daily dose of each fatty acid administered is within the range of 1 mg to 100 g per day.

2. A method of mitigating the ill effects of smoking, wherein there is administered to a smoker, a formulation of one or more the n-6 EFAs selected from the group consisting of GLA, DGLA and AA, and/or one or more of the n-3 EFAs selected from SA, 20:4n-3, EPA, DPA and DHA, so that the daily dose of each fatty acid is within the range 1 mg to 100 g per day.

3. The method according to claim 1 or claim 2 wherein the formulation comprises both n-6 essential fatty acids and n-3 essential fatty acids.

4. The method according to claim 1 or claim 2 wherein the formulation is a nutritional supplement in oil, powder, whip, foam, granule, flake or mousse form and wherein the fatty acids are present in a concentration of from 0.001 to 50% by weight in total.

5. The method according to claim 1 or claim 2 wherein the formulation is a topical preparation for absorption through the skin, in ointment, lotion, cream, oil, stick or patch form and wherein the fatty acids are present in a concentration of from 0.001 to 50% by weight in total.

6. A method of treating untimely ageing of the skin in smokers, wherein there is administered to a smoker, a formulation comprising:

(a) at least one of the n-6 essential fatty acids selected from the group consisting of gamma-linolenic acid (GLA), dihomo-gamma-linolenic acid (DGLA) and arachidonic acid (AA); or (b) at least one n-3 essential fatty acid selected from the group consisting of stearidonic acid (SA), 8,11,14-17-eicosatetraenoic acid (20:4n-3), eicosapentaenoic acid (EPA), docosapentaenoic acid (DPA) and docosahexaenoic acid (DHA); or (c) a mixture of (a) and (b);

so that the daily dose of each fatty acid is within the range 1 mg to 100 g per day.

7. The method according to claim 6 wherein the formulation comprises both n-6 essential fatty acids and n-3 essential fatty acids.

8. The method according to claim 6 wherein the formulation is a nutritional supplement in oil, powder, whip, foam, granule, flake or mousse form and wherein the fatty acids are present in a concentration of from 0.001 to 50% by weight in total.

9. The method according to claim 6 wherein the formulation is a topical preparation for absorption through the skin, in ointment, cream lotion, oil, stick or patch form and wherein the fatty acids are present in a concentration of from 0.001 to 50% by weight in total.

* * * * *